(12) United States Patent
Fujiwara (10) Patent No.: US 6,406,477 B1
(45) Date of Patent: Jun. 18, 2002

(54) INTRAMEDULLARY NAIL

(75) Inventor: Hiroo Fujiwara, Kurashiki (JP)

(73) Assignee: Koi Inc., Okayama (JP)

( * ) Notice: Subject to any disclaimer, the term of this patent is extended or adjusted under 35 U.S.C. 154(b) by 0 days.

(21) Appl. No.: 09/767,075

(22) Filed: Jan. 22, 2001

(30) Foreign Application Priority Data

Jul. 27, 2000 (JP) ....................................... 2000-231416

(51) Int. Cl.⁷ ............................................. A61B 17/72
(52) U.S. Cl. ....................................................... 606/67
(58) Field of Search ............................. 606/62, 63, 64, 606/67, 68, 72

(56) References Cited

U.S. PATENT DOCUMENTS

| | | | |
|---|---|---|---|
| 4,827,917 A | * 5/1989 | Brumfield | 128/42 YZ |
| 4,875,475 A | * 10/1989 | Comte et al. | 128/924 Y |
| 5,176,681 A | 1/1993 | Lawes et al. | |
| 5,531,748 A | 7/1996 | de la Caffiniere | |
| 6,106,528 A | * 8/2000 | Durham et al. | 606/64 |
| 6,123,708 A | * 9/2000 | Kilpela et al. | 606/62 |
| 6,228,086 B1 | * 5/2001 | Wahl et al. | 606/67 |
| 6,235,031 B1 | * 5/2001 | Hodgeman et al. | 606/64 |

FOREIGN PATENT DOCUMENTS

| | | |
|---|---|---|
| JP | 10066698 A | 10/1998 |
| JP | 11137566 A | 5/1999 |

* cited by examiner

Primary Examiner—Eduardo C. Robert
(74) Attorney, Agent, or Firm—Paul & Paul (57) ABSTRACT

A lag screw for connecting a bone portion separated from the femur, by fracture, to the main portion thereof is fixedly secured in the separated bone portion and extends through main portion of the femur. A nail member is installed in the femur in order to fix the lag screw to the femur. The lag screw is secured in the nail member by a set screw inserted into an outer end of the nail member. In order to prevent the rotation of the separated bone portion about the lag screw, an auxiliary connector is inserted through the nail member between the lag screw and the set screw. The lag screw is clamped by the set screw via a spacer for transmitting a clamping force.

4 Claims, 7 Drawing Sheets

INTRAMEDULLARY NAIL

BACKGROUND OF THE INVENTION

1. Field of the Invention

The present invention relates to an intramedullary nail used for an intramedullary nailing procedure.

2. Description of the Related Art

The intramedullary nail is mainly used for treating a fracture of the proximal portion of the femur such as an intertrochanteric fracture or a subtrochanteric fracture by pulling the proximal bone portion, separated from the femur by the fracture, to the femur to compress and fix them.

The intramedullary nail includes a nail member inserted into the femur from one end thereof, and a lag screw extending through the nail member and connected to the bone portion separated by the fracture. The lag screw includes engaging means for engaging the separated bone portion at the forward end thereof, and is fixedly supported on the nail member by a set screw inserted into a threaded hole formed in the outer end of the nail member. The nail member is formed with a through hole extending diagonally across the proximal portion thereof so that the forward end of the lag screw inserted into the through hole may be screwed into the bone portion separated by fracture such as the caput of bone positioned at a diagonally upward side.

In the treatment of the fractured proximal portion of the femur, the first step is to insert the nail member in the proximal end of the femur and install it in the medullary cavity thereof. Then, a locking screw can be inserted, if necessary, such that it extends across the medullary cavity and the distal portion of the nail member thereby fixing the nail member at a predetermined position in the femur. As the next step, the engaging means (threaded portion) at the forward end of the lag screw is passed through the through hole of the nail member into the portion of the caput of bone positioned more proximal than the fractured portion thereby to secure the separated caput to the lag screw. After that, the separated caput of the femur is pulled by the lag screw in such a manner as to press the separated caput against the main portion of the femur. When the caput of the femur comes to be positioned adjacent to the main portion thereof, the set screw is inserted into a threaded fixing hole of the nail member so that the forward end of the set screw engages the peripheral surface of the lag screw thereby to secure the lag screw to the nail member.

However, the separated portion of the bone such as the fractured caput, which is secured only to a single bone connector such as a lag screw, is liable to rotate about the bone connector. The rotation of the separated bone portion hinders the separated bone portion from being coapted to the main portion of the bone. Therefore, this can result in a problem that the healing time of the fracture is increased or that the fracture line is displaced before the separated bone portion is coapted to the main portion. In the case where the degree of rotation is high, the muscle surrounding the separated portion of the bone such as the caput may be damaged.

In order to prevent such a rotation of a separated bone portion, it is required to connect the separated bone portion of the femur and the main portion thereof by additionally providing an auxiliary connector extending across the nail member to the separated bone portion. However, the auxiliary connector cannot pass across through the nail member because of the presence of a set screw extending longitudinally inside of the nail member from one end thereof for securing the bone connector to the nail member.

SUMMARY OF THE INVENTION

Accordingly, it is an object of the present invention to obviate the problem in the prior art described above to provide an intramedullary nail allowing a bone connector and an auxiliary connector to be inserted into a nail member for preventing the rotation of a bone portion separated from a main portion of a femur by fracture and located on the proximal side of the fractured portion, thereby to promote the healing of the fractured portion.

In order to achieve the object described above, in accordance with a first aspect of the present invention, there is provided an intramedullary nail which includes a bone connector for connecting a bone portion separated from a main portion of a bone by fracture to the main portion, the bone connector extending through the main portion and secured in the separated bone portion; a nail member installed in the main portion of the bone for fixing the bone connector to the main portion, the bone connector extending through the nail member; a set screw inserted into an outer end of the nail member for securing the bone connector in the nail member; an auxiliary connector extending through the nail member between the bone connector and the set screw; and a spacer for transmitting a clamping force from the set screw to the bone connector thereby to clamp the bone connector.

In accordance with a second aspect of the present invention, there is provided an intramedullary nail which includes a bone connector for connecting a bone portion separated from a main portion of a femur by fracture to the main portion, the bone connector extending through the main portion and secured in the separated bone portion; a nail member installed in the main portion of the femur for fixing the bone connector to the main portion, the bone connector slidably inserted through the nail member; a set screw inserted into a set hole for securing the bone connector in the nail member, the set hole formed in an outer end of the nail member and extending longitudinally of the nail member; an auxiliary connector extending through the nail member between the bone connector and the set screw; and a spacer for transmitting a clamping force from the set screw to the bone connector without interfering with the auxiliary connector, thereby to clamp the bone connector.

In accordance with a third aspect of the present invention, there is provided an intramedullary nail which includes a bone connector for connecting a bone portion separated from a main portion of a bone by fracture to the main portion, the bone connector extending through the main portion and secured in the separated bone portion; a nail member installed in the main portion of the bone for fixing the bone connector to the main portion, the bone connector extending through the nail member; a set screw inserted into an outer end of the nail member for securing the bone connector in the nail member; and an auxiliary connector extending through the nail member and arranged in a position where the auxiliary connector is free from the set screw.

In the intramedullary nail described above, the spacer includes two legs extending in spaced relation with each other, and the auxiliary connector extends through the nail member between the two legs. Preferably, the bone connector has grooves formed on a peripheral surface thereof for the two legs of the spacer to engage.

In the above-mentioned intrammedullary nail, the set screw may include a boss extending toward the spacer, which boss passes through the spacer to engage a groove formed on a peripheral surface of the auxiliary connector.

Since the auxiliary connector extending through the nail member between the bone connector and the set screw is provided and the spacer for transmitting the clamping force is interposed between the set screw and the bone connector, the auxiliary connector extending to the separated bone portion through the nail member prevents the rotation of the separated bone portion. Also, the clamping force of the set screw inserted to the outer end of the nail member is transmitted to the bone connector over the auxiliary connector via the spacer, thereby permitting the bone connector to be secured in the nail member.

BRIEF DESCRIPTION OF THE DRAWINGS

The above and other objects, features, and advantages of the present invention will be made more apparent from the following description of the preferred embodiments thereof with reference to the accompanying drawings, wherein.

DESCRIPTION OF THE PREFERRED EMBODIMENTS

Preferred embodiments of an intramedullary nail according to the present invention will be described below with reference to the accompanying drawings.

Figure 1:
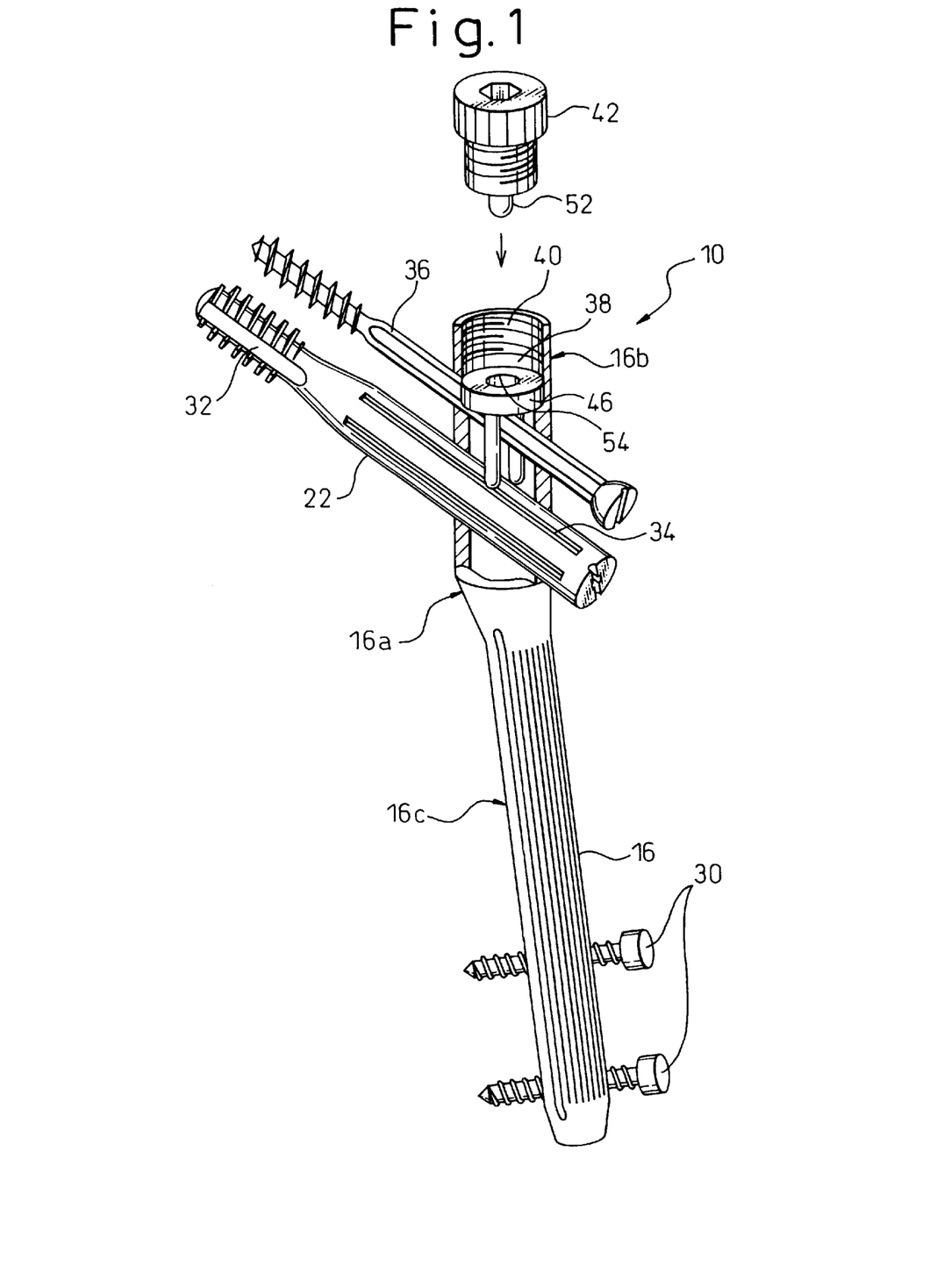
FIG. 1 is a partly sectional perspective view of one embodiment of an intramedullary nail according to the present invention.
Figure 2:
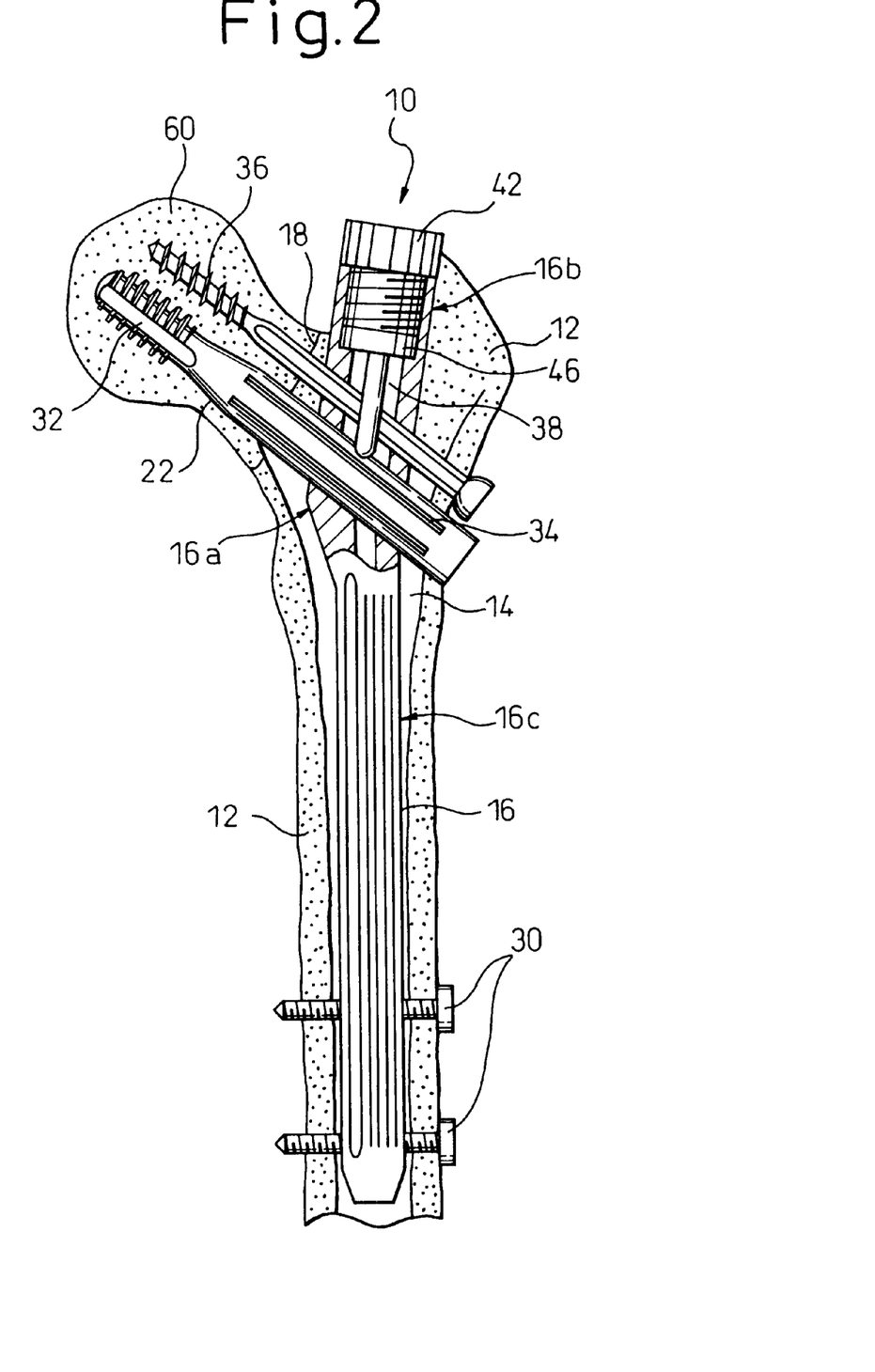
FIG. 2 is a partly sectional view illustrating the whole intramedullary nail shown in FIG. 1 used to fix the fractured portions of the femur.
Figure 3:
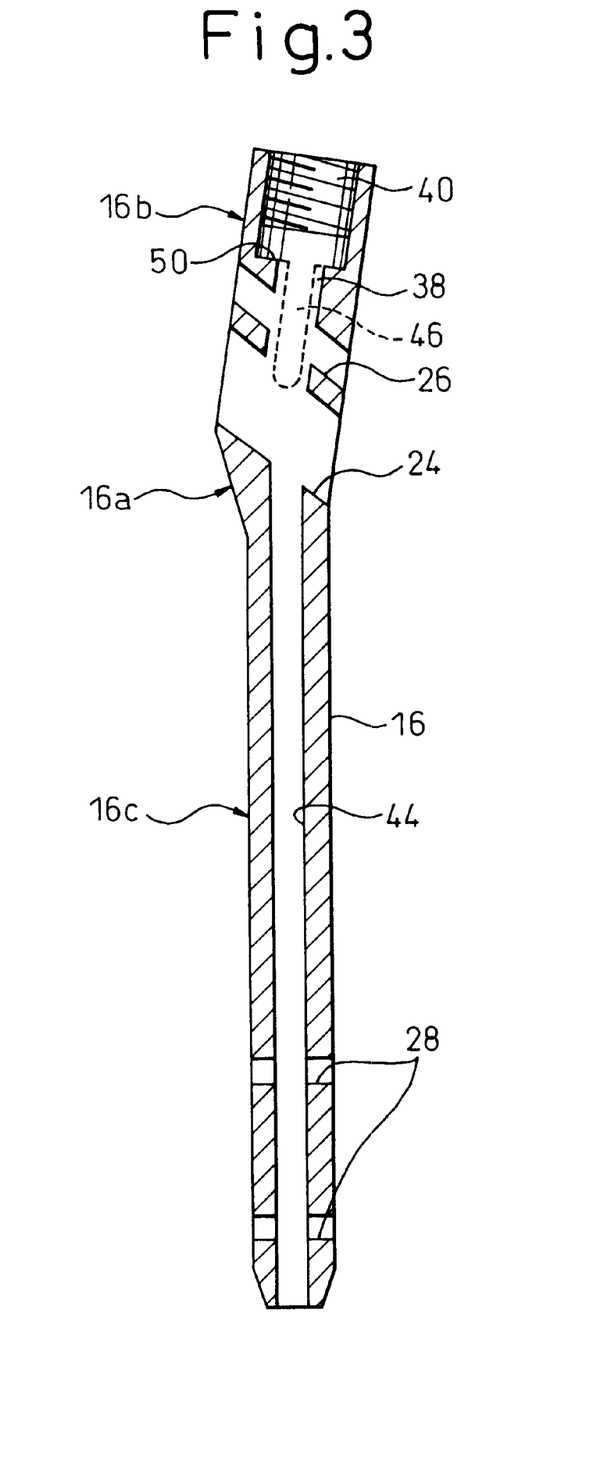
FIG. 3 is a sectional view of the nail member shown in FIG. 1.

FIG. 1 is a partly sectional perspective view of one embodiment of an intramedullary nail according to the present invention, and FIG. 2 is a partly sectional view illustrating the whole intramedullary nail shown in FIG. 1 used to fix the fractured portions of the femur. FIG. 3 is a sectional view of the nail member shown in FIG. 1.

Referring to FIGS. 1 and 2, the intramedullary nail 10 according to the present invention includes a rod-shaped nail member 16 inserted into the inner cavity (medullary cavity) 14 of a femur 12 from one end of the femur 12, and a lag screw 22, i.e. a bone connector for connecting to the main portion of the femur 12 a bone portion 20 separated from the main portion of the femur 12 by the fracture along a fracture line 18.

Specifically, referring to FIG. 3, the nail member 16 includes a proximal portion 16b, an distal portion 16clonger than the proximal portion 16b, and a bent portion 16a located at a boundary between them. As best shown in FIG. 3, the proximal portion 16b is formed with two through holes, a main through hole 24 and an auxiliary through hole 26, extending in parallel diagonally across the nail member 16 in the neighborhood of the bent portion 16a of the nail member 16. The proximal portion 16b of the nail member 16 is formed in a large size sufficient to accommodate the through holes 24, 26, while the distal portion 16c is formed in a small size suitable for the shape of the inner cavity (medullary cavity) 14 of the femur 12 in order to facilitate the insertion of the distal portion 16 into it. Fixing through holes 28 extending orthogonal to the axis of the distal portion 16c are formed at an end of the distal portion 16c of the nail member 16. Locking screws 30 are inserted across the shaft of the femur 12 (the body of the femur 12) into the fixing through holes 28 in order to securely fix the nail member 16 to the shaft of the femur 12.

In the embodiment of the intramedullary nail 10 shown in FIGS. 1 and 2, the bone connector is the lag screw 22. The lag screw 22 has engaging means 32 such as a threaded portion at the forward end thereof for engaging the bone portion 20 separated from the main portion of the femur 12, and the proximal portion of the lag screw 22 is formed with a plurality of grooves 34 extending on the peripheral surface thereof along the axis of the lag screw 22 (in the lag screw 22 shown in FIGS. 1 and 2, four grooves 34 are disposed on the peripheral surface of the lag screw 22 at intervals of 90° around the axis of the lag screw 22). The lag screw 22 is inserted into the femur 12 with the engaging means 32 thereof directed ahead, and further slidably inserted into the main through hole 24 of the nail member 16 thereby to penetrate into the separated bone portion 22. Thus, the lag screw 22 is fixedly secured in the separate bone portion 20 by causing the engaging means 32 at one end of the lag screw to engage the separated bone portion 20. Finally, the separated bone portion 20 is fixed to the main portion of the femur 12 by securing the other end of the lag screw 22 to the main through hole 24 of the nail member 16 installed in the femur 12.

The intramedullary nail 10 according to the present invention further includes an auxiliary connector 36 slidably inserted through an auxiliary through hole 26 located in the nail member 10 as shown in FIGS. 1 and 2. The auxiliary connector 36, like the lag screw 22, i.e. the bone connector, is arranged in such a position as to pass through the main portion of the femur 12 while being passed into the separated bone portion 20 thereof.

The auxiliary connector 36 and the bone connector arranged in this way form two fixed axles extending from the nail member 16 to the separated bone portion 20 thereby to prevent the separated bone portion 20 from rotating about the bone connector (the lag screw 22). However, the auxiliary connector 36 can be used for other purposes than preventing the rotation of the separated bone portion 20.

A set hole 38, which extends longitudinally in the nail member 16 from one end thereof across the auxiliary through hole 26 to the main through hole 24 and has at least a portion threaded, is formed at the outer end (proximal end) of the nail member 16. A set screw 42 is screwed into the set hole 38 for applying the clamping force to the lag screw 22 inserted into the main through hole 24.

Further, in order to allow a guide rod (not shown) to be used for facilitating the insertion into the inner cavity 14 of the femur 12, an inner hole 44 for the guide rod 44 may be formed along the longitudinal axis of the nail member 16 as shown in FIG. 3. In such a case, the set hole 38 in the proximal portion 16b of the nail member 16 constitutes a part of the inner hole for the guide rod.

In the intramedullary nail 10 according to the present invention, the auxiliary connector 36 extends through the nail member 16 at a location between the set screw 42 screwed into the outer end of the nail member 16 and the lag screw 22, i.e. a bone connector. Therefore, in order to allow the set screw 42 to apply a clamping force to the lag screw 22 over the auxiliary connector 36, a spacer 46 for transmitting a clamping force is interposed between the set screw 42 and the lag screw 22.

Figure 4:
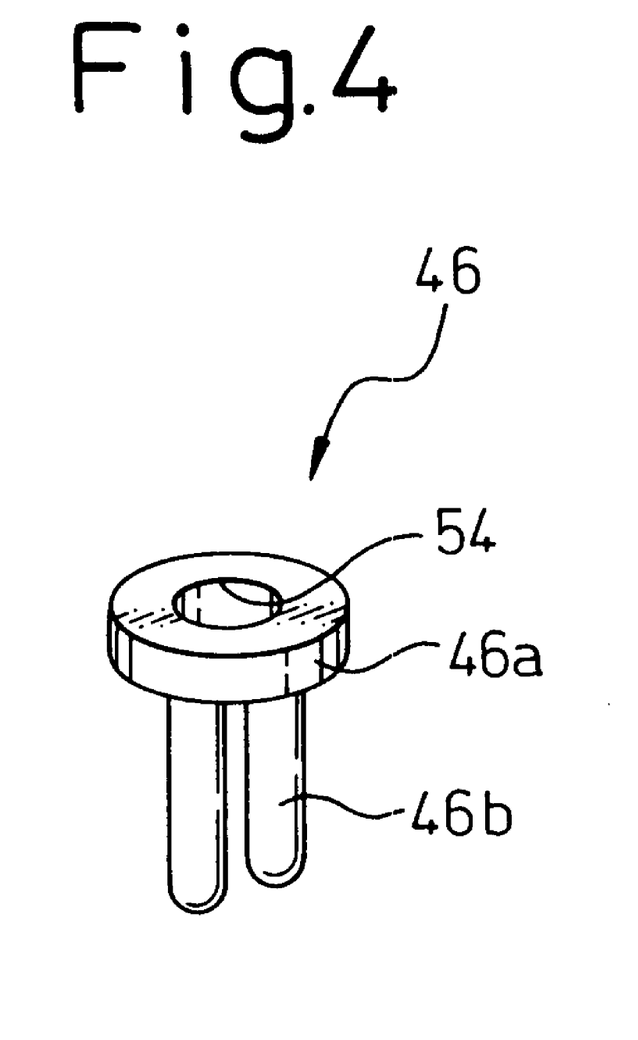
FIG. 4 is a perspective view of one embodiment of a spacer for transmitting a clamping force.
Figure 5:
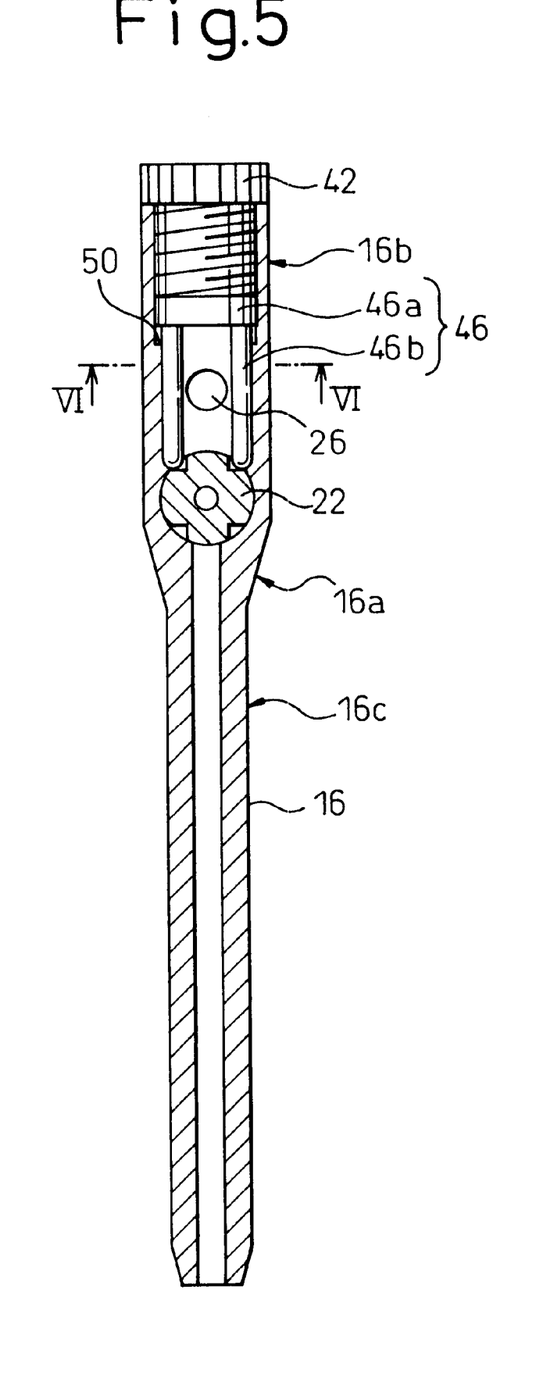
FIG. 5 is a partly sectional view of the intramedullary nail for explaining the principle on which the clamping force is applied by a set screw to a lag screw via the spacer and by which the rotation of the lag screw is prevented.
Figure 6:
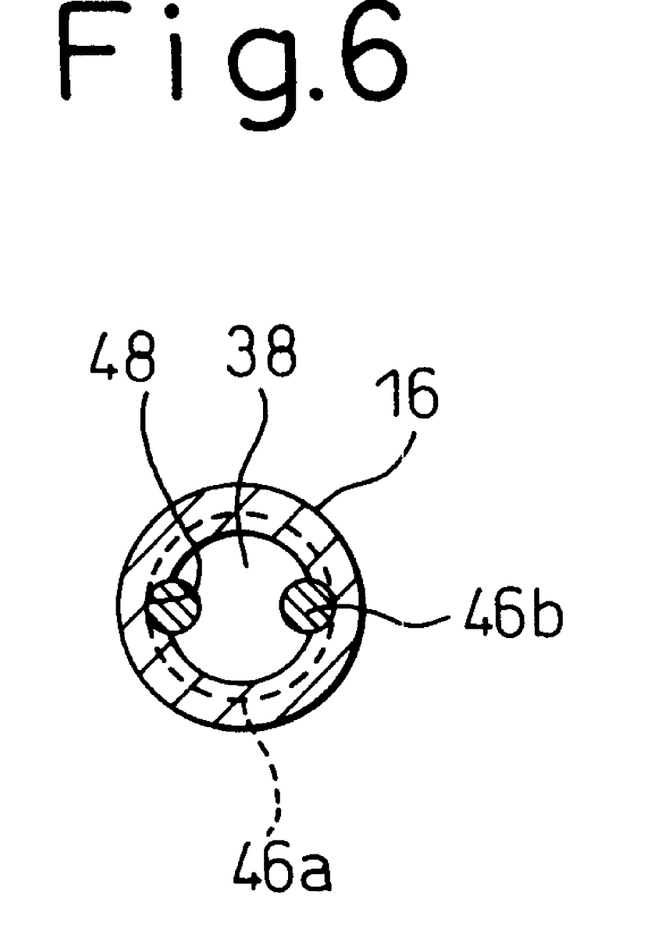
FIG. 6 is a sectional view taken along line VI—VI of FIG. 5.

FIG. 4 is a perspective view of one embodiment of the spacer 46. FIG. 5 is a partly sectional view of the intramedullary nail for explaining the principle on which the clamping force is applied by the set screw to the lag screw 22 via the spacer 46 and the rotation of the lag screw 22 is prevented. FIG. 6 is a sectional view taken along line VI—VI of FIG. 5.

The spacer 46 shown in FIG. 4 includes a body 46a and two legs 46b extending from the body 46a in spaced relation with each other.

As shown in FIG. 5, when the set screw 42 is placed on the spacer 46 inserted into the set hole 38 and is screwed into it, the set screw 42 engaged with the threaded portion of the set hole 38 abuts against the body 46a. Thus, the set screw 42 pushes down the whole of the spacer 46 and the lower ends of the legs 46b come into engagement with the grooves 34 of the lag screw 22, thereby securing the lag screw 22 in the nail member 16 while at the same time preventing the rotation of the lag screw 22. Even in the case where the grooves 34 are not formed on the periphery surface of the lag screw 22, the lag screw 22 can be secured in the nail member 16 by being clamped between the nail member 16 (particularly the surface of the main through hole 24) and the spacer 46 due to the friction between the lower ends of the legs 46b of the spacer 46 and the peripheral surface of the lag screw 22.

The auxiliary connector 36 inserted into the auxiliary through hole 26, on the other hand, can pass through the nail member 16 by way of the space defined between the two spaced legs 46b of the spacer 46. As shown in FIG. 5, preferably, the diameter of the portion of the set hole 38 in the neighborhood of the main through hole 24 is rendered smaller than that of the portion thereof engaged by the set screw 42, and guide grooves 48 for the legs 46b are formed on the inner surface of the set hole 38 as shown in FIG. 6. Such guide grooves 48 can prevent the spacer 46 from being rotated by the rotation of the set screw 42 when the set screw 42 is screwed into the set hole 38. Also, the portion of the set hole 38 where the diameter thereof changes defines a shoulder 50 as shown in FIG. 3, thereby limiting the downward movement of the body 46a of the spacer 46. Thus, the movable range of the spacer 46 is limited such that the lower ends of the legs 46b are suspended in the main through hole 24 even when the spacer 46 moves to its lowest position. This enables the forward end of the leg screw 22 to come into contact with the legs 46b of the spacer 46 during the insertion of the lag screw 22, thereby moving the spacer 46 upward.

In the case where it is desirable to securely hold the auxiliary connector 26 in the nail member 16, a boss 52 may be formed at the forward end of the set screw 42 and inserted through an opening 54 formed in the body 46a of the spacer 46 to abut against the auxiliary connector 36, as shown in FIG. 1. In this way, the set screw 42 is inserted in the set hole 38 and engaged with the threaded portion thereof, so that the boss 52 of the set screw 42 comes into contact with the auxiliary connector 36, which makes it possible to securely hold the auxiliary connector 36 in the nail member 16. Further, in order to prevent the rotation of the auxiliary connector 36, a longitudinally extending groove may be formed on the auxiliary connector 36 to be engaged by the boss 52 of the set screw 42.

Figure 7:
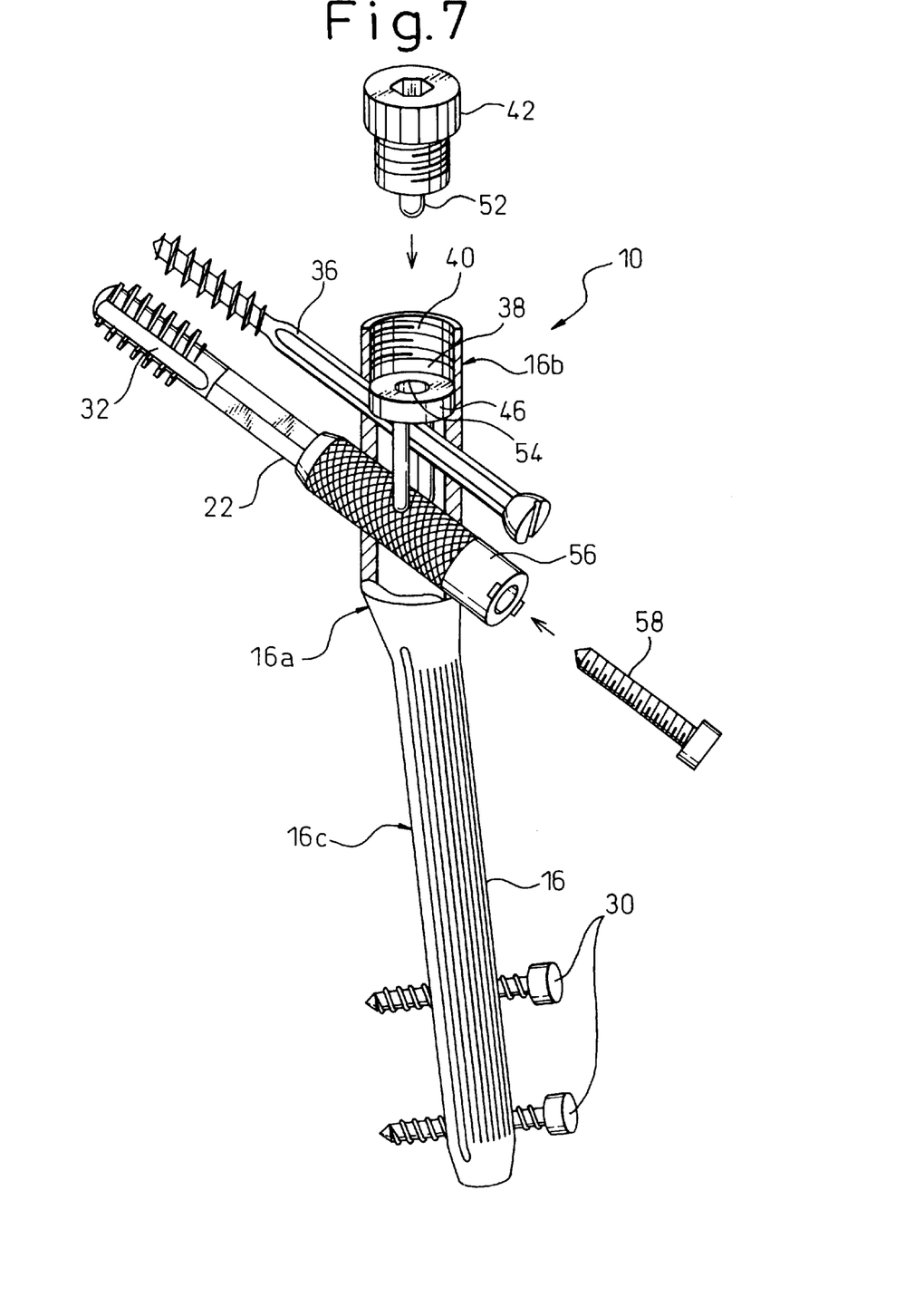
FIG. 7 is a partly sectional perspective view of another embodiment of an intramedullary nail according to the present invention.

FIG. 7 is a perspective view of another embodiment of an intramedullary nail 10 according to the present invention which is similar to that shown in FIG. 1 except that the bone connector is of such a type that the compression force can be easily exerted on the separated portion of bone.

The bone connector shown in FIG. 7 includes a sleeve 56 inserted into the main through hole 24 of the nail member 16, and the lag screw 22 is inserted into the sleeve 56. The proximal end of the lag screw 22 is formed with a threaded hole (not shown) in the axial direction, and the forward end of the pulling screw 58 for pulling the lag screw 22 is inserted into the same threaded hole. The head of the proximal end of the pulling screw 58 is in contact with the annular shoulder formed on the inner surface of the proximal end of the sleeve 56. By rotating the pulling screw 58, the lag screw 22 can be pulled in such a direction as to pull the separated bone portion 20 toward the remainder (main portion) of the femur 12 and apply a compression force to it. The peripheral surface of the sleeve 56 shown in FIG. 7 is serrated to enhance a frictional engagement with the spacer 46. Alternatively, the peripheral surface of the sleeve 56 can of course be formed with grooves, like the lag screw 22 shown in FIG. 1, which are adapted to engage the legs 46b of the spacer 46.

Components of the intramedullary nail described above are preferably made of pure titanium, a titanium alloy, the cobalt-nickel alloy or a similar biocompatible material.

In the shown embodiment, the spacer 46 is shown as a separate member from the set screw 42. However, the set screw 42 and the spacer 46 may be integrated with each other.

A method of using the intramedullary nail 10 shown in FIG. 1 will be now described.

The femur 12, as shown in FIG. 2, includes a caput 60 at an end thereof and an inner cavity (medullary cavity) 14 in the shaft thereof. The fracture related to the caput 60 of the femur 12 is liable to occur in the neck portion of caput 60 having a thin root, for example, at the position indicated by the fracture line 18 shown in FIG. 2. In the case of such a fracture, if the separated bone portion (caput 60) is fixed by a single bone connector like the lag screw 22 as in the prior art, the separated bone portion 20 could rotate about the bone connector (i.e. the lag screw 22), often having an adverse effect on the healing of the fractured portion. In view of this, the intramedullary nail 10 according to the invention is provided with an auxiliary connector 36 substantially parallel to the axis of a bone connector, and the separated bone portion 20 and the main portion of the femur 12 are connected and fixed to each other by use of these two connectors.

First, after a guide rod (not shown) is inserted into the femur 12 along the inner cavity 14 thereof, a hole is formed in the femur 12 by drilling along the guide rod. The nail member 16 is inserted into the inner cavity 14 while being guided by the guide rod until it reaches a predetermined position as shown in FIG. 2. Then, by passing the locking screws 30 across the shaft of the femur 12 through the fixing through holes 28, the nail member 16 is fixed at a predetermined position of the femur 12. After the nail member 16 is fixed at a predetermined position, the guide rod is removed from the inner cavity 14 of the femur 12.

As the next step, a guide pin (not shown) is inserted from the side wall of the femur 12 into the forward end of the caput 60 across the femur 12 through the main through hole 24 of the nail member 16. After drilling a hole in the femur 12 along the guide pin, the lag screw 22 is inserted into the femur 12 through the main through hole 24 of the nail member 16 with the engaging means (threaded portion) 32 of the lag screw 22 directed forward while being guided by the guide pin until the engaging means 32 of the lag screw 22 reaches the separated bone portion 20 (caput 60). Thus, the lag screw 22 is fixedly secured in (engaged with) the bone portion 20 by the engaging means 32. After that, the lag screw 22 is pulled in such a direction that the engaging means 32 approaches the nail member 16 to compress the fractured portions, and the separated bone portion 20 is pulled into close proximity with the main portion of the femur 12.

As the next step, in order to prevent the separated bone portion from rotating about the lag screw 22, the auxiliary connector 36 is screwed from the side wall of the femur 12 across the femur 12 and through the auxiliary through hole 26 of the nail member 16 to the bone portion 20. As a result, the nail member 16 installed in the shaft of the femur 12 and the separated bone portion 20 are connected to each other by the two connectors, i.e. the bone connector (lag screw 22) and the auxiliary connector 36, with the result that the separated bone portion 20 cannot rotate.

As the last step, the spacer 46 is inserted into the set hole 38 formed at the outer end of the nail member 16, and the set screw 42 is screwed over the spacer 46. In the process, the auxiliary connector 36 extending laterally through the nail member 16 is adapted to pass between the legs 46b of the spacer 46. By tightening the set screw 42, the legs 46b of the spacer 46 are forced to come into engagement with the grooves 34 of the lag screw 22, so that the lag screw 22 is securely held in the nail member 16 while the rotation of the lag screw 22 is prevented. Specifically, in the intramedullary nail 10 according to the invention, the clamping force of the set screw 42 is transmitted to the lag screw 22 over the auxiliary connector 36 extending across the nail member 16 between the set screw 42 and the lag screw 22 by way of the spacer 46 thereby to secure the lag screw 22 in the nail member 16. The legs 46b of the spacer 46 are guided along the guide grooves 48 formed in the inner surface of the set hole 38. Therefore, the legs 46b of the spacer 46, which cannot be rotated by rotation of the set screw 42, never interfere with the auxiliary connector 36. The guide pin is removed after the lag screw 22 is secured in the nail member 16.

As described above, the intramedullary nail prevents the rotation of the separated bone portion 20 (caput 60) and the relative displacement of the fractured portions before the separated bone portion 20 and the main portion of the femur 12 are fixed and the fractured portions are successfully coapted to each other.

The present invention was described above with reference to the intramedullary nail 10 used for fixing the fractured portions positioned in the neighborhood of the caput 60 of the femur 12 as an example. However, the present invention is equally applicable to any intramedullary nail for fixing fractured portions positioned in the neighborhood of the caput of other bones such as the humerus.

In addition, another type of an intramedullary nail can achieve the effect of preventing a rotation of a separated bone portion. One embodiment of this type of the intramedullary nail may include a bone connector extending through a femur to a bone portion separated from a main portion of the femur and secured to the separated bone portion for connecting the separated bone portion to the main portion of the femur, a nail member through which the bone connector extends and which is installed in the femur for fixing the bone connector to the main portion of the femur, a set screw inserted into an outer end of the nail member for securing the bone connector to the nail member, and an auxiliary connector extending through the nail member and arranged in a position where the auxiliary connector is free from the set screw (for example, under the bone connector or in a position farther away from the set screw than the bone connector).

It will thus be understood from the foregoing description that, according to the present invention, a separated bone portion can be fixed to a main portion of the femur by two connectors, i.e. a bone connector and an auxiliary connector, and therefore the fractured portions are not displaced by the rotation of the separated bone portion, thereby making it possible to promote the healing of the fracture. Also, since a clamping force of the set screw can be applied to the bone connector by a spacer for transmitting the clamping force over the auxiliary connector extending across the nail member at a position between the set screw and the bone connector, secure holding of the bone connector in the nail member is not sacrificed.

What is claimed is:

1. An Intramedullary Nail, comprising:
   a bone connector for reunifying a fractured bone, wherein the fractured bone comprises a first bone portion and a second bone portion, said bone connector capable of extending through said first bone portion and secured in said second bone portion;
   a nail member capable of being installed in said first bone portion, said bone connector extending through said nail member;
   a set screw inserted into an outer end of said nail member, said set screw securing said bone connector in said nail member;
   a spacer disposed against the set screw for transmitting a clamping force from said set screw to said bone connector, said spacer having two legs extending therefrom, in a direction opposite the set screw, in spaced relation to each other, said legs engaging said bone connector; and
   an auxiliary connector extending through said nail member between said two legs of the spacer and between said bone connector and said set screw.

2. The Intramedullary Nail according to claim 1, wherein said bone connector has grooves formed on a peripheral surface thereof with which grooves the two legs of said spacer engage.

3. The Intramedullary Nail according to claim 1, wherein said set screw includes a boss extending toward said spacer to engage a groove formed on a peripheral surface of said auxiliary connector.

4. An Intramedullary Nail, comprising:
   a bone connector for reunifying a fractured femur, wherein the fractured femur comprises a first femur portion and a second femur portion, said bone connector capable of extending through said first femur portion and secured in said second femur portion;
   a nail member capable of being installed in said first femur portion, said nail comprising an end having a set bore disposed along its longitudinal axis and at least two transverse bores, said bone connector slideably inserted through one of said at least two transverse bores;
   a set screw inserted into said set bore for securing said bone connector in said nail member;

an auxiliary nail connector extending through another of the at least two transverse bores of said nail member between said bone connector and said set screw; and a spacer disposed against the set screw for transmitting a clamping force from said set screw to said bone connector without interfering with said auxiliary connector, said bone connector having one or more grooves formed on a peripheral surface thereof, said spacer having two legs extending in a direction opposite the set screw, in spaced relation to each other, said two legs engaging said grooves, said auxiliary connector extending through said nail member between said two legs.

* * * * *